United States Patent
Tanaka

(10) Patent No.: US 6,846,624 B1
(45) Date of Patent: Jan. 25, 2005

(54) EXPRESSION CLONING PROCESS FOR GENE CODING FOR A ZINC-BINDING PROTEIN

(76) Inventor: Toshio Tanaka, 2673-2, Fujikata, Tsu-shi, Mie (JP)

( * ) Notice: Subject to any disclaimer, the term of this patent is extended or adjusted under 35 U.S.C. 154(b) by 0 days.

(21) Appl. No.: 09/068,461

(22) PCT Filed: Nov. 5, 1996

(86) PCT No.: PCT/JP96/03233

§ 371 (c)(1),
(2), (4) Date: May 6, 1998

(87) PCT Pub. No.: WO97/17438

PCT Pub. Date: May 15, 1997

(30) Foreign Application Priority Data

Nov. 7, 1995 (JP) .............................. 7-288784

(51) Int. Cl.[7] .............................. C12Q 1/68; C12Q 1/02
(52) U.S. Cl. .............................. 435/6; 435/29
(58) Field of Search ....................... 435/6, 29; 530/350, 530/810; 536/23.1; 436/6, 71.2, 320.1, 476

(56) References Cited

U.S. PATENT DOCUMENTS

| | | | | |
|---|---|---|---|---|
| 5,665,865 A | * | 9/1997 | Lerner et al. ............. | 530/387.3 |
| 5,679,548 A | * | 10/1997 | Barbas et al. ............. | 435/69.6 |
| 5,759,803 A | * | 6/1998 | Kaelin et al. ............. | 435/69.1 |
| 5,821,070 A | * | 10/1998 | Lee et al. ................. | 435/7.23 |
| 5,891,418 A | * | 4/1999 | Sharma ..................... | 424/1.69 |
| 5,917,018 A | * | 6/1999 | Thogerson et al. ......... | 530/350 |

FOREIGN PATENT DOCUMENTS

WO          89/09777          10/1989

OTHER PUBLICATIONS

Reardan et al. Antibodies against metal chelates. Nature, vol. 316:265–267, 1985.*

Stemmer et al. Selection of an active single chain Fv antibody from a protein linker library prepared by enzymatic inverse PCR. BioTechniques vol. 14(2):256–265, 1993.*

Hoffman et al. Binding of antibodies and other proteins to nutrocellulose in acidic, basic, and chaotropic buffers. Anal. Biochem. vol. 198:112–118, Apr. 1991.*

Khoo et al. Purification and properties of rat cysteine–rich intestinal protein. Biochemical Journal. vol. 299:445–450, Sep. 1993.*

Sunderman et al. Xenopus lipovitellin 1 is a zn (2+) —and cd(2+) —binding protein. Molecular Reproduction And Develepment. vol. 42:180–187, Oct. 10, 1995.*

Pohl et al. Plaque–liftr testing of expression vector lamb-dagt11 with gold–labeled immunoglobulins. Anal. Biochem. vol. 175:414–421, Mar. 1988.*

Stone et al., "Targeted RNA Fingerprinting: The Cloning of Differentially–Expressed cDNA GB, Fragments Enriched for Members of the Zinc Finger Gene Family" Nucleic Acids Research, Oxford University Press, Surrey, vol. 22, No. 13, 1994, pp 2612–2618.

Skolnik et al., "Cloning of Pl3 Kinase–Associated p85 Utilizing a novel method for Expression/Cloning of Target Proteins for Receptor Tyrosine Kinases," *Cell* (Apr. 5, 1991), vol. 65, pp. 83–90, XP–002100383.

* cited by examiner

*Primary Examiner*—Terry McKelvey
(74) *Attorney, Agent, or Firm*—Foley & Lardner LLP

(57) ABSTRACT

The present invention provides a process for efficiently cloning DNA that codes for ligand-binding protein. This process is characterized in that a host containing DNA inserted into an expression vector is plate-cultured, said DNA is expressed, the protein that is produced is transferred to a film from said plate by placing said film in contact with said plate, said film is peeled from said plate, labeled ligand is added to said film to bind said ligand to said protein, the label bound to said protein is detected, and DNA is isolated from clones on the plate corresponding to locations on the film that demonstrated a positive reaction.

9 Claims, No Drawings

EXPRESSION CLONING PROCESS FOR GENE CODING FOR A ZINC-BINDING PROTEIN

TECHNICAL FIELD

The present invention relates to an expression cloning process of a gene coding for a ligand-binding protein. According to the present invention, a gene that codes for a ligand-binding protein having useful biological activity can be cloned efficiently.

BACKGROUND ART

Cell growth and differentiation occur by a signal transmission mechanism in which extracellular signals act on the genetic program of cells. The majority of genes in which transcription is initially modified by signal transmission are genes that code for transcription regulation factors. Those substances having molecules that are responsible for this type of signal transmission are called ligands.

Ligands are molecules that specifically bind with protein, and the proteins that bind with ligands are referred to as ligand-binding proteins. Examples of ligands include various drugs, nucleotides and metal ions, while examples of ligand-binding proteins include proteins generically referred to as receptors or enzymes and various other types of biologically active proteins.

Ligands are believed to be involved in the signal transmission of various biological activities as a result of binding with ligand-binding proteins.

Metal ions in particular are known to be ligands that fulfill important roles in the body. For example, zinc ions have been clearly shown to bind with numerous transcription regulatory factors and act on the expression of their functions. In addition, transcription regulatory factors are known to be involved in generation, differentiation, inflammation, cell growth and so forth. However, transcription regulatory factors are only present in the body in trace amounts, thus making their purification and the analysis of their molecular structure difficult.

Some transcription regulatory factors are known to have a zinc finger structure. Attar, R. M. et al. (Mol. Cell. Biol. (1992) 12, 2432–2443) reported the cloning of a gene coding for a protein having a zinc finger structure that binds with a serum response factor by using a serum response factor DNA probe.

Methods which utilize the homology of an amino acid or nucleotide sequence based on its characteristic basic structure are not considered to be able to be used for cloning of genes that code for zinc finger proteins. Although the majority of zinc finger proteins that have already been cloned were acquired based on the partial amino acid sequence of an intranuclear receptor or other purified protein, other known zinc finger proteins include those identified as proteins that bind to the transcription regulatory region, such as the GATA transcription factor group (Tsai, S. F., et al., Nature (1989) 339, 446–451), and those determined to be zinc finger proteins as a result of structural analysis of the chromosome translocation site of leukemia cells, such as Evans, T. et al. (Cell (1989) 58, 877–855) and Ttg-1 gene (Mcguire, E. A. et al., Mol. Cell. Biol. (1989) 9, 2124–2132). Similarly, the PML gene was also newly identified from analysis of the chromosome translocation site of APL, while PML-RAR, which is the product of fusion by chromosome translocation with the zinc finger, retinoic acid receptor (RAR), is thought to be intimately involved in transcription regulation of leukemia cells (Kakizuka, A. et al., Cell (1991) 66, 663–674, de The, H. et al., Cell (1991) 66, 675–684). In this manner, although zinc finger proteins have important functions, there are as of yet no direct methods having high specificity that involve binding of ligand, namely zinc ion, without limiting the target DNA.

DISCLOSURE OF THE INVENTION

As a result of earnestly studying a process for efficiently cloning a gene that codes for ligand-binding protein, the inventors of the present invention found that ligand-binding protein can be efficiently and simply acquired by directly identifying ligand-binding protein by using a DNA library containing various genes, expressing that DNA library and utilizing the binding properties of ligands to ligand-binding protein, thereby leading to completion of the present invention.

Thus, the present invention provides a novel process for cloning a gene that codes for ligand-binding proteins with high efficiency that could not be achieved with the methods of the prior art. More specifically, the present invention provides a novel process for efficiently and simply cloning a gene that codes for zinc ion-binding protein.

In order to solve the above-mentioned problems, the present invention provides an expression cloning process for a gene that codes for ligand-binding protein characterized in that, a host containing DNA inserted into an expression vector is plate-cultured, said DNA is expressed, the protein that is produced is transferred to a film from said plate by placing said film in contact with said plate, said film is peeled from said plate, labeled ligand is added to said film to bind said ligand to said protein, the label bound to said protein is detected, and DNA is isolated from host clones on the plate corresponding to locations on the film that demonstrated a positive reaction.

According to the present invention, it is easy to obtain various ligand-binding proteins from various cells and tissues, thereby enabling screening of pharmaceuticals by using these ligand-binding proteins as target molecules.

Best Mode for Carrying Out the Invention

In the carrying out of the present invention, to begin with, a DNA library, comprising expression vectors into which DNA has been inserted, is prepared. All cells and tissues in which DNA coding for the target ligand-binding protein is desired to be cloned can be used as DNA acquisition sources, examples of which include brain, thyroid, lung, heart, thymus, pancreas, spleen, kidney, adrenal, intestinal, skeletal muscle, bone marrow, epithelial, placental, vascular, blood and other tissues as well as cells originating in these tissues. Although the DNA acquired from these cells and tissues may be either cDNA or genomic DNA, cDNA is used preferably. In the case of cDNA, mRNA is purified from the target cells or tissue, after which cDNA is synthesized by reverse transcriptase and the synthesized product can be used as cDNA. The above-mentioned cells and tissue may be normal cells and tissue, or in the case of focusing on ligand-binding protein involved in a specific disease, the cells and tissue may be in the corresponding disease state. Moreover, cells and tissue from artificially created pathological states, namely from various pathological models, can also be used. In addition, these cells and tissue may be from fetuses or adults, and from human or non-human animals.

Preparation of a DNA library can be performed in accordance with known, routine methods. Any vectors routinely used for preparation of a DNA library can be used as expression vectors for composing a DNA library, examples of which include phage vectors and plasmid vectors. These vectors contain ordinary, known expression control sequences such as promoters and enhancers, and are able to express the DNA contained therein. Moreover, it is preferable that they also contain an expression induction sequence. Examples of phage vectors include λZAP and λgt11.

Any host can be used for the host that composes the DNA library provided it is routinely used in DNA libraries and can be infected by a vector. Moreover, those hosts that allow control of expression induction are preferable. *Escherichia coli* such as Y1090 is a specific example of such a host. Expression vectors are preferably those that express the inserted DNA in the presence of an expression inductor, and examples of expression induction sequences for this purpose include the lac promoter of the lac operon and its modified tac promoter. In addition, isopropyl β-D-thiogalactoside (IPTG) is used as its corresponding expression inductor.

Next, host cells transformed by an expression vector containing DNA that composes the above-mentioned DNA library are inoculated onto a solid plate medium and cultured. Culturing should be performed under ordinary, known conditions so that the DNA library is favorably expressed inside the host cells. As a result, a plaque is formed in the case of using a phage vector, for example, for the expression vector. As a result of this culturing, in the case of an expression vector that does not require induction of expression, protein is produced in the plaque portion due to expression of the DNA contained therein. By then bringing a film in contact with the above-mentioned plate, the protein that is produced is transferred to the film. An expression inductor is added in the case the expression vector requires an expression inductor for expression of DNA. When adding an expression inductor, the expression inductor may be added in advance directly to the culture liquid, or it may be impregnated into the film. After adding an expression inductor to the film, said film is brought in contact with the above-mentioned plate. Consequently, the expression inductor is transferred from the film to the plate medium, production of protein coded for by said DNA is induced, and that protein is transferred to the above-mentioned film.

The film used in the process of the present invention is preferably a film that allow impregnation of expression inductor and transfer of protein, and routinely used blotting films, examples of which include nitrocellulose film and Nylon film, are used.

Next, the film may be washed to remove any media components and cells, etc. transferred from the plate and then treated with a protein denaturant. Guanidine hydrochloride, urea or various reducing reagents and so forth can be used as the protein denaturant. Protein denaturation is performed by treating the above-mentioned film with a buffer such as Tris-HCl buffer containing the above-mentioned denaturant. This denaturation is performed to allow the target protein to easily bind with ligand by temporarily destroying undesirable high-order structures of proteins formed inside the microorganism. Next, the above-mentioned protein denaturant is washed off and removed by washing the film with a washing solution such as Tris-HCl buffer. Next, protein on the film is regenerated by treating the film with a regenerating solution.

Next, after washing the film to remove the regenerating solution, a solution containing labeled ligand is applied to the film. Any ligand can be used provided it binds with protein, examples of which include various drugs, nucleotides and metal ions. The ligand is preferably a zinc ion, a preferable example of which is an isotope ($^{65}$Zn) having radioactivity.

As a result, if a host clone containing DNA that codes for ligand-binding protein (positive clone) is present on the above-mentioned plate, the location of the positive clone on the plate can be determined by detecting the label. Various labels or detection means used in biological assays can be used for the label and detection means. If the ligand is a metal ion, for example, a radioisotope of that metal ion can be used as a labeled ligand. In addition, fluorescent labels, biotin labels, enzyme labels and antibody labels can also be used according to the properties of the ligand.

Any routine detection means can be used depending on the label that is used. For example, if the radioisotope of a metal ion is used for the labeled ligand, a positive spot can be identified by autoradiography or using a bioimage analyzer after which a positive clone can be identified on the above-mentioned plate at the location corresponding to that spot. In addition, image analysis and so forth is another example of a label detection means that is used depending on the above-mentioned labels.

Positive clones obtained in this manner can be purified from the above-mentioned plate medium by repeatedly reacting in later processes. Once a positive clone is identified in this manner, the vector is isolated from the cells of the positive clone in accordance with routine methods followed by cutting out the target DNA.

INDUSTRIAL APPLICABILITY

According to the process of the present invention, DNA coding for ligand-binding proteins can be cloned extremely efficiently from various types of normal and pathological cells and tissues, thereby enabling the screening of pharmaceuticals by using these ligand-binding proteins as target molecules.

EXAMPLES

Although the following provides a detailed explanation of the present invention through its examples, the present invention is not limited to those examples.

EXAMPLE 1

Uni-ZAPXR library (Stratagene) was used for the human lung expression cDNA library. This cDNA library was infected into *Escherichia coli* (XL1-Blue, Stratagene) which was then inoculated onto a square plate measuring 12 cm on a side at the rate of roughly $1\times10^4$ pfu by mixing with top agarose. The plate was incubated for about 3 to 4 hours at 42° C. After the plaque had reached a certain size, a nitrocellulose film impregnated with 20 mM isopropyl β-D-thiogalactoside (IPTG) was placed on the plate after which the plate was additionally incubated for roughly 4 hours at 37° C. to allow the protein to be expressed and transferred onto the film. After marking the film and plate, the film was peeled from the plate and washed for 1 hour at 4° C. in TBST solution (25 mM Tris-HCl (pH 7.5), 150 mM NaCl, 0.05% Tween 20).

The protein on the film was denatured with solution A (6 M guanidine HCl, 30 mM Tris-HCl (pH 7.4) and 5 mM dithiothreitol (DTT)). After removing the guanidine by rinsing in solution B (30 mM Tris-HCl (pH 7.4) and 150 mM NaCl), the protein on the film was regenerated with solution C (30 mM Tris-HCl (pH 7.4), 150 mM NaCl and 2 mM DTT). The film was again rinsed in solution D (10 mM Tris-HCl (pH 7.4) and 150 mM NaCl) and then incubated for 15 minutes in solution E (10 mM Tris-HCl (pH 7.4), 150 mM NaCl and 10 pCi/ml $^{65}$Zn). Following incubation, the film was promptly washed for 10 minutes with solution F (10 mM Tris-HCl (pH 7.4) and 150 mM NaCl) and this washing was repeated three times.

After allowing the film to completely dry, autoradiography was performed and an X-ray film (Kodak XAR-5) was exposed for 4 days. Moreover, the above-mentioned procedure was repeated for the positive plaque obtained to obtain single clones and a single nucleotide sequence was determined for those clones. As a result, the nucleotide sequence was clearly shown to contain a portion of the PLZF (promyelocytic leukemia zinc finger) gene coding for a kruppel-like zinc finger protein. PLZF is a zinc ion-binding transcription regulatory factor that has several zinc finger motifs on its C terminal side.

EXAMPLE 2

Another single clone was obtained using the same method as Example 1 and its nucleotide sequence was determined. As a result, this nucleotide sequence was clearly shown to contain a portion of the transcription regulatory factor, Jun-interacting factor (Jif)-1 gene. Therefore, in order to investigate the binding of Jif-1 with zinc ion, Jif-1 was cloned according to the PCR method and expressed in the form of a fused protein with glutathione-S-transferase (GST) using *Escherichia coli*. SDS-PAGE was performed on the GST-Jif-1 fused protein or lysed cells of *Escherichia coli* in which GST protein was expressed followed by transfer to a nitrocellulose film. Since GST-Jif-1 fused protein bound with zinc ion while GST protein did not, Jif-1 was clearly determined to bind with zinc ion.

What is claimed is:

1. A process for isolating a vector that contains a gene encoding a protein having a zinc finger structure or which binds zinc, comprising culturing a host cell on a culture plate, wherein the host cell contains an expression vector which contains an uncharacterized DNA, expressing the vector to produce a protein, transferring the protein in the host cell to a film by contacting the host cell on the culture plate with the film, peeling the film from the culture plate, treating the protein on the film with a protein denaturant, washing the film, regenerating the protein on the film with a regenerating solution, adding a labeled zinc ion to the film which can bind to the protein, detecting the labeled zinc ion bound to the protein, and isolating the vector containing the uncharacterized DNA from host cells at a location on the culture plate which corresponds to the location of the protein-bound labeled zinc ion on the film.

2. The process as set forth in claim 1, wherein said uncharacterized DNA is cDNA.

3. The process as set forth in claim 1, wherein said expression vector is able to only express inserted DNA in the presence of an expression inductor, and said DNA is expressed by adding said expression inductor.

4. The process as set forth in claim 1, wherein said labeled zinc ion is a radioisotope.

5. The process as set forth in claim 1, wherein said detecting is by autoradiography.

6. The process as set forth in claim 1, wherein said uncharacterized DNA is obtained from a cell or a tissue expressing said uncharacterized DNA encoding a target protein having a zinc finger structure.

7. The process as set forth in claim 6, wherein said cell or said tissue is selected from the group consisting of brain, thyroid, lung, heart, thymus, pancreas, spleen, kidney, adrenal, intestinal, skeletal muscle, bone marrow, epithelium, placenta, vascular and blood.

8. The process as set forth in claim 6, wherein said cell or said tissue is in a disease state.

9. The process as set forth in claim 6, wherein said cell or said tissue is healthy.

* * * * *